United States Patent
Santar et al.

(10) Patent No.: US 6,706,695 B2
(45) Date of Patent: Mar. 16, 2004

(54) ANTILIPEMIC FORMULATION

(75) Inventors: Ivan Santar, Predklasteri (CZ); Frantisek Kiss, Brno (CZ); Jiri Briestensky, Cernilov (CZ)

(73) Assignee: Alpenstock Holdings Limited, Sallynoggin (IE)

( * ) Notice: Subject to any disclaimer, the term of this patent is extended or adjusted under 35 U.S.C. 154(b) by 156 days.

(21) Appl. No.: 09/764,340

(22) Filed: Jan. 19, 2001

(65) Prior Publication Data

US 2001/0003742 A1 Jun. 14, 2001

Related U.S. Application Data

(63) Continuation of application No. PCT/IE99/00070, filed on Jul. 21, 1999.

(30) Foreign Application Priority Data

| Jul. 21, 1998 | (IE) | ................................................ | S980594 |
| Jul. 21, 1998 | (IE) | ................................................ | S980595 |
| Jul. 21, 1998 | (IE) | ................................................ | S980596 |
| Jul. 21, 1998 | (IE) | ................................................ | S980597 |
| Jul. 21, 1998 | (IE) | ................................................ | S980598 |
| Jul. 21, 1998 | (IE) | ................................................ | S980599 |

(51) Int. Cl.$^7$ ............................................. A61K 31/715
(52) U.S. Cl. ........................... 514/54; 514/57; 424/451; 424/464
(58) Field of Search ................................. 424/451, 464; 514/54, 57

(56) References Cited

U.S. PATENT DOCUMENTS 5,593,682 A    1/1997    Papas et al. ................. 424/401

FOREIGN PATENT DOCUMENTS

| WO | WO95/12620 | 5/1995 |
| WO | WO98/00180 | 1/1998 |
| WO | WO98/33822 | 8/1998 |

OTHER PUBLICATIONS

Patent Abstracts of Japan, vol. 8, No. 126, Jun. 13, 1984 JP 59 038204 A (Shiyouwa Sangyo KK), Mar. 2, 1984.
Patent Abstracts of Japan, vol. 9, No. 12, Jan. 18, 1985 JP 59 163323 A (Shiyouwa Sangyo KK), Sep. 14, 1984.
Database Accession No. 123:218422, Susumu et al, "Hypolipemics containing acidic . . . ", JP 07 188038 A (Kao Corp), Jul. 25, 1995.
Database Accession No. 115:270441, Dinggang et al, "Isolation, purification, analysis, and . . . ", (Zhongguo Yaoke . . . ), 1991.
Patent Abstracts of Japan, vol. 14, No. 531, Nov. 21, 1990 JP 02 221224 A (Tatsuaki Yamaguchi) Sep. 4, 1990.
Briestensky et al, STN Chemical Abstracts, vol. 10, No. 110, "Production of oxidized . . . ", XP002120226, Apr. 3, 1989.
Domszy et al, Chitin Nat. Technol. Muzzarelli et al, XP00212113 "Ionic interactions between . . . ", pp. 331–336, 1986.
Nagyvary, Nutrition Reports International, vol. 2, No. 5, "The hypolipidemic activity . . . ", pp. 677–684, 1979.
Henkel, FDA Consumer, "Keeping cholesterol under control", pp. 24–27, Jan.–Feb. 1999.
Michaeli et al, SCIENCE, vol. 166, "Localization of Antigenic Determinants in the . . . ", pp. 1522–1524, 1969.

*Primary Examiner*—Phyllis G. Spivack
*Assistant Examiner*—C. Delacroix-Muirheid
(74) *Attorney, Agent, or Firm*—Jacobson Holman PLLC

(57) ABSTRACT

An antilipemic composition, particularly to achieve a lowering of cholesterol levels comprises a biocompatible anionic polysaccharide material containing non-sulphated glucuronic acid.

37 Claims, No Drawings

US 6,706,695 B2

ANTILIPEMIC FORMULATION

This application is a continuation of PCT/IE99/00070 filed on Jul. 21, 1999.

The invention relates to an antilipemic composition and in particular to a composition for lowering cholesterol.

As outlined in a recent publication [Facts About Cholesterol: The Plague of Plaque, FDA Consumer magazine, January–February 1999], cholesterol, C27H45OH, is a monohydric alcohol, a sterol, widely distributed in animal tissues. It can be synthesized in the liver and is a normal constituent of bile. It is the principal constituent of most gallstones. It is important in metabolism, serving as a precursor of various steroid hormones (e.g., sex hormones, adrenal corticoids). In most individuals, however, an elevated blood level of cholesterol constitutes an increased risk of developing coronary heart disease (CHD). Scientific evidence has established that lowering definitely elevated blood cholesterol (specifically, blood levels of low-density lipoprotein cholesterol) reduces the risk of heart attacks due to CHD.

Cholesterol is needed for some important body functions, but when present in excessive amounts, it can injure blood vessels and cause heart attacks and stroke. The body needs cholesterol for digesting dietary fats, making hormones, building cell walls, and other important processes. The bloodstream carries cholesterol in particles called lipoproteins that are like blood-borne carriers delivering cholesterol to various body tissues to be used, stored or excreted. But too much of this circulating cholesterol can injure arteries, especially the coronary ones that supply the heart. This leads to accumulation of cholesterol-laden "plaque" in vessel linings, a condition called atherosclerosis. If a blood clot completely obstructs a coronary artery affected by atherosclerosis, a heart attack (myocardial infarction) or death can occur.

Lipoproteins are conjugated proteins consisting of simple proteins combined with lipid components: cholesterol, phospholipid, and triglyceride. Most plasma lipids do not circulate in an unbound state but are chemically linked with proteins. Analysis of their concentrations and proportions in the blood can provide important clues as to their role in certain diseases, particularly cardiovascular abnormalities, hypertension, atherosclerosis, and coronary artery disease. Lipoproteins are classified as very low-density (VLDL), low-density (LDL), intermediate-density (IDL) and high-density (HDL). It is thought that individuals with high blood levels of HDL are less predisposed to coronary heart disease than those with high blood levels of VLDL or LDL.

Two types of lipoproteins and their quantity in the blood are main factors in heart disease risk:

Low-density lipoprotein (LDL)—This "bad" cholesterol is the form in which cholesterol is carried into the blood and is the main cause of harmful fatty buildup in arteries. The higher the LDL cholesterol level in the blood, the greater the heart disease risk.

High-density lipoprotein (HDL)—This "good" cholesterol carries blood cholesterol back to the liver, where it can be eliminated. HDL helps prevent a cholesterol buildup in blood vessels. Low HDL levels increase heart disease risk.

One of the primary ways LDL cholesterol levels can become too high in blood is through eating too much of two nutrients: saturated fat, which is found mostly in animal products, and cholesterol, found only in animal products. Saturated fat raises LDL levels more than anything else in the diet. Several other factors such as heredity, weight, exercise, age and gender, and stress also affect blood cholesterol levels.

Cholesterol levels may be decreased by several factors, including diet, avoiding smoking, and avoiding anabolic steroids. Drugs commonly used to control cholesterol include lovastatin, niacin, gemfibrozil, clofibrate, probucol, and bile-acid resins (cholestyramine, colestipol). The decision of which drug to prescribe is based on factors such as degree of cholesterol lowering desired, side effects, and cost.

A number of substances have been applied to reduce cholesterol levels in blood. One of the early therapies involved heparin, a polysaccharide isolated from natural sources. However, the isolation process is costly and heparin therapy is therefore rather expensive at efficient doses. This led to the introduction of sulphated polysaccharides known as heparinoides. The additional sulphatation and the presence of the OSO3H groups brought about a lower efficiency and a higher toxicity compared to heparin.

Another group of polymers applied as antilipemics have been anion exchange resins of varying degree of basicity, exchanging Cl-ions for anions of bile acids. Cholestyramine and colestipol bind bile acids in the intestine and prevent their recycling through the liver. Because the liver needs cholesterol to make bile, it increases its uptake of cholesterol from the blood. These drugs are, in most cases, not resorbed from the gastrointestinal tract, but can adversely affect resorption of other drugs. Due to the rather high daily doses (up to 30 g) they may also cause gastric problems.

Antilipemic properties have also been observed for certain hormones such as gestagens. Their complex hormonal activity precludes, however, their common use in antilipemic therapy.

Nicotinic acid (niacin) lowers total and LDL cholesterol and raises HDL cholesterol. It also can lower triglycerides. Because the dose needed for treatment is about 100 times more than the recommended daily allowance for niacin and thus can potentially be toxic, the drug must be taken under a doctor's care.

Fibric acid derivatives such as gemfibrozil and fenofibrate can also increase HDL levels, but are used mainly to lower triglycerides.

The most prominent cholesterol drugs are in the statin family, an array of powerful treatments that includes lovastatin, fluvastatin, pravastatin, simvastatin), cervastatin, and atorvastatin. Statins work by interfering with the cholesterol-producing mechanisms of the liver and by increasing the capacity of the liver to remove cholesterol from circulating blood. Adverse side effects have also been reported recently for antilipemic drugs based on statins such as fluvastatin.

The invention in particular involves the use of polyanhydroglucuronic acids and salts thereof The term polyanhydroglucuronic acid and salts there of as used herein also includes copolymers thereof, especially with anhydroglucose. This is hereinafter referred to as PAGA.

Co-pending patent application PCT IE98/00004 describes particular polyanhydroglucuronic acids and salts thereof and a method of preparing such compounds. In particular therefore, the term polyanhydroglucuronic acids and salts thereof includes the acids and salts referred to in this co-pending application.

STATEMENTS OF INVENTION

We have now found an important antilipemic effect, comparable with that of statins, in non-sulphated polysaccharides containing glucuronic acid in the polymer chain. Glucuronoglucanes, notably those bound with 1,4 β glycosidic bonds in the form of PAGA as prepared, particularly, according to PCT IE/98/00004, their salts, complex salts, and intermolecular complexes thereof with cationic polymer counterions such as, notably, gelatine or chitosan, when applied perorally, preferably in the form of tablets, pellets, granules, or microspheres, display a significant cholesterol lowering activity at relatively low daily doses of 15 to 100 mg per kg body weight.

In tests on volunteers it has been observed that the effect of increasing HDL cholesterol level, and reducing both LDL/ VLDL and total cholesterol levels was comparable with a control group of patients treated with fluvastatin with no adverse side effects reported.

It may be hypothesised that the mechanism of this effect is related to the increased supply of glucuronic acid and their oligomers to the organism during absorption and degradative clearance of the orally administered glucuronoglucane.

One advantage of the therapy based on the invention is due to the inherent biocompatibility, lack of toxicity and virtual absence of adverse side effects inherent to PAGA salts and intermolecular complexes, especially when prepared according to the method of, and as explained in, PCT IE/98/00004. This together with the low doses required reduce the potential risks to the patient compared with other types of antilipemic drugs.

A final advantage resides in the fact that PAGA salts and intermolecular complexes, especially when prepared according to the method of the earlier PCT IE/98/00004 can, in addition to their own therapeutic function, simultaneously serve as a vehicle for other antilipemic agents with potential synergic effects such as notably phospholipides, e.g. soya or egg derived lecithins, α-tocoferol, or ascorbic acid.

According to the invention there is proved an anlilpemic composition including a biocompatible anionic polysaccharide material containing non-sulphated glucuronic acid.

Preferably the polysaccharide is derived from a starch, cellulose or gum, or is of microbial origin.

In a particularly preferred embodiment the polysaccharide material is polyanhydroglucuronic acid, biocompatible salts thereof, copolymers thereof or a biocompatible intermolecular complex polymer thereof.

In an embodiment of the invention the biocompatible intermolecular polymer complex is a complex of:

an anionic component comprising a linear or branched polysaccharide chain containing glucuronic acid; and a non protein cationic component comprising a linear or branched natural, semi-synthetic or synthetic oligomer or polymer.

Preferably at least 5% of the basic structural units of the anionic component are glucuronic acid.

In one embodiment the cationic component contains nitrogen that either carries a positive charge or wherein the positive charge is induced by contact with the polysaccharidic anionic component.

In this case preferably the cationic component is selected from derivatives of acrylamide, methacrylamide and copolymers thereof.

Preferably the cationic component is selected from polyacrylamide, copolymer of hydroxyethylmethacrylate and hydroxypropylmetacrylamide, copolymers of acrylamide, butylacrylate, maleinanhydride and/or methylmetacrylate.

The cationic component may be a cationised natural polysaccharide.

In this case preferably the polysaccharide is a starch, cellulose or gum. The gum is preferably guargumhydroxypropyltriammonium chloride.

In another embodiment the cationic component is a synthetic or semi-synthetic polyamino acid.

Preferably the cationic component is polylysin, polyarginin, or α,β-poly-[N-(2-hydroxyethyl)-DL-aspartamide].

Alternatively the cationic component is a synthetic anti-fibrinolytic. The anti-fibrinolytic may be a hexadimethrindibromide (polybren).

In another embodiment the cationic component is a natural or semi-synthetic peptide.

Preferably the peptide is a protamine, gelatine, fibrinopeptide, or derivatives thereof.

Alternatively the cationic component is an aminoglucane or derivatives thereof.

In this case the aminoglucane may be fractionated chitin or its de-acetylated derivative chitosan.

The aminoglucane may be of microbial origin or is isolated from the shells of arthropods such as crabs.

In an particularly preferred embodiment the anionic component is polyanhydroglucuronic acid [PAGA].

Preferably the polyanhydroglucuronic acid and salts thereof contain in their polymeric chain from 8 to 30 per cent by weight of carboxyl groups, at least 80 per cent by weight of these groups being of the uronic type, at most 5 per cent by weight of carbonyl groups, and at most 0.5 per cent by weight of bound nitrogen.

Ideally the polyanhydroglucuronic acid and salts thereof contain in their polymeric chain at most 0.2 per cent by weight of bound nitrogen.

The molecular mass of the polymeric chain of the anionic component is preferably from $1 \times 10^3$ to $3 \times 10^5$ Daltons.

Ideally the molecular mass of the polymeric chain of the anionic component ranges from $5 \times 10^3$ to $1.5 \times 10^5$ Daltons.

In one embodiment the content of carboxyl groups is in the range of from 12 to 26 per cent by weight, at least 95 per cent of these groups being of the uronic type.

Preferably the anionic component contains at most 1 per cent by weight of carbonyl groups.

In a preferred embodiment the carbonyl groups are intra- and intermolecular 2,6 and 3,6 hemiacetals, 2,4 hemialdals and C2–C3 aldehydes.

In another embodiment the cationic component is gelatine.

In a further embodiment the cationic component is chitosan.

The composition may include at least one biocompatible biologically active substance.

The composition may include at least one pharmaceutically active adjuvant.

The adjuvant may be an antilipemic agent.

The antilipemic agent may be a phospholipid.

The composition may be in a form for oral administration such as in the form of a tablet, pellet, capsule, granule, or microsphere.

We have now found that by preparing polymeric intermolecular complexes (IMC) of glucuronoglucanes, notably microdispersed PAGA, prepared especially according to PCT IE 98/00004 it is possible to enhance the haemostatic effect of the final products on this basis and the properties of the temporary wound cover formed after the haemostasis is achieved such as its flexibility and resistance to cracking on movable parts of the body.

It is also possible to upgrade physicomechanical properties of the final products on this basis. Such IMCs make it possible to prepare application forms whose manufacture from a pure PAGA or their simple salts is extremely difficult. Such application forms includes non-woven textile-like structures or polymeric films. To modify or upgrade the physical mechanical properties it is sufficient to use even a relatively small amount of polymeric counterion while it is possible to obtain suitable application properties within a broad concentration range of the components. The ratio of the glucuronoglucane to polymeric counterion can be 0.99:0.01 to 0.01:0.99.

Another advantage of glucuronoglucane based IMCs is the possibility to control their biological properties such as varying the degree of haemostatis, resorption time, or immunomodulative properties, and the like.

Polymeric cations suitable to form IMCs with glucuronoglucanes prepared for example according to PCT IE 98/00004 may roughly be subdivided to the following groups:

1. Synthetic biocompatible nitrogen-containing oligomers and polymers.
    a) Derivatives of acrylamide and methacrylamide and their copolymers [such as polyacrylamide, copolymer of hydroxyethylmetacrylate and hydroxypropylmetacrylamide, copolymer of acrylamide, butylacrylate, maleinanhydride, and methylmetacrylate, and the like], or else cationised natural polysaccharides such as starches, celluloses, or gums such as guargumhydroxypropyltriammonium chloride.
    b) Synthetic or semi-synthetic polyaminoacids such as polylysin, polyarginin, $\alpha,\beta$-poly-[N-(2-hydroxyethyl)-DL-asparamide. Synthetic antifibrinolytics hexadimethrindibromide (polybren) can also be included in this group.
2. Natural or semi-synthetic peptides such as gelatine, protamines, or fibrinopeptides, and their derivatives.
3. Natural aminoglucanes such as fractionated chitin and its de-acetylated derivative chitosan, of microbial origin or isolated from the shells of arthropods such as crabs.

In preparing IMCs on the basis of PAGA according to the invention these three groups of substances can be combined to obtain required properties of the final product.

In general it can be said that IMCs using substances from 1a and 1b would preferably be used to prepare various types of highly absorbant biocompatible dressing materials in the form of nonwovens, films, plasters, and pads.

IMCs using the substances from 2 and 3 may serve as efficient haemostatic agents for internal applications in the microfibrillar form, in the microdispersed form as dusting powders, in the form of films, granules, tablets or nonwoven textile-like structures. Those preparations also display antiadhesive properties.

We have also found out that in the form of film-like cell culture matrices the latter IMCs incorporating PAGA and salts thereof as prepared according to PCT IE 98/00004 have a favourable effect on the growth of fibroblasts and keratinocytes.

While it is also possible to create IMCs using structural scleroproteins of the collagen type as disclosed in WO 9800180A, it is preferable to use the above mentioned groups of substances because of the possibility of contamination of the final product by telopeptides, viruses or pyrogens. Collagen can affect in an uncontrolled manner, the immune response of the organism because formation of antibodies can be provoked by any portion of the collagen structure even though the main determinants occur in the terminal regions of the collagen macromolecule. Removal of telopeptides only partially solves the antigenicity problem (Michaeli et al: Science, 1969, 166, 1522).

By preparing IMCs according to the invention it is possible to essentially enhance properties of the originally prepared glucoronoglucanes such as 1,4 $\beta$ PAGA. For instance an intermolecular complex salt of PAGA and gelatine in one single production step can be used to prepare final products in the form of a non woven, film, microdispersed granules, or dispersions. In contrast to collagen, suitably hydrolysed gelatine is well tolerated, has no toxicity or side effects and it is a much less costly raw material. We have found out that this complex has very good haemostatic properties being about 40% higher than the original PAGA calcium sodium salt. This is despite the fact that the gelatine itself only displays a haemostatic effect after an addition of thrombin [Schwartz S. I. et al.: Principles of Surgery, St. Louis: McGraw Hill Colo., 1979, p. 122–123]. In this case the absorption in the organism can be controlled by changing the composition of the complex within the range from tens of hours to several months. With an advantage this complex with a higher haemostatic efficiency can be used as an embolisation or microembolisation product. It can also be used to prepare haemostatic layers of highly absorbent multi-layer dressings or resorbable plasters, though more costly polybren or protamines could also be applied.

An important advantage of these IMCs is the fact that the compounds can be prepared within a single manufacturing operation using the hydrolytic process described in PCT IE 98/00004 which makes these products cost effective.

These IMCs can further be modified by biologically active and/or biologically acceptable substances. Because the IMCs prepared by the present procedure are either of a microdispersed or microfibrillar nature, the active substances tend to be bound uniformly and also are uniformly released in the organism without the need for other adjuvants such as microcrystalline waxes or stearates. However, the addition of such adjuvants is not excluded.

Biologically active substances which can be incorporated into the IMC may involve, for instance, antibiotics carrying at least a weak positive charge in the molecule such as cephalosporins (cephotaxin), arninoglycosides (neomycin, gentamycin, amikacin), penicillins (tikarcilin) or macrolides (erythromycin, clarithromycin) and the like.

In cases where the calcium/sodium salt of PAGA or its IMC complexes according to the invention are used as microembolisation or embolisation agents in regional chemotherapy of malign tumours, suitable types of cytostatics such as adriamycin or derivatives of 1,4-diaminoanthrachinone can be incorporated. It is also possible to use the IMCs as detaching ligands for platinum(II) based cytostatics.

Biologically acceptable substances used for modification of the IMCs include, for instance, glycerol and its polymers (polyglycerols); mono, di, and certain triglycerides; polyethyleneglycols; monopropyleneglycol; block copolymers of polyethyleneoxides and polypropyleneoxides (Pluronic); starches; cyclodextrines; polyvinylalcohols; cellulose and its derivatives; in general, substances that, in the concentrations used, are not irritating or toxic for the living organism while being capable of further optimising the physicomechanical properties of the final product based on the IMCs according to the invention.

DETAILED DESCRIPTION

The invention will be more clearly understood from the following description thereof given by way of example only.

EXAMPLES OF POLYMER COMPLEXES OF GLUCORONOGLUCANES

Example 1

Material
- long-fibre cotton—medicinal cotton wool oxidised by $N_xO_y$ (proprietary)
- $C_6OOH$ 18.8% b/w
- ash content <0.1% b/w
- $\Sigma C=O$ 0.6% b/w
- 20% solution $Na_2CO_3$ (Lachema, a.s. Neratovice)
- $CaCl_2.6H_2O$ anal.grade (Lachema, a.s. Neratovice)
- demineralised water 2 µS
- ethanol, synthetic rectified conc. 98% (Chemopetrol Litvinov, a.s.)
- acid acetic anal.grade (Lachema, a.s. Neratovice)
- $H_2O_2$ anal.grade 30% (Lachema, a.s. Neratovice)
- N-HANCE 3000 guargumhydroxypropyltriammoniumchloride (Aqualon—Hercules)

Equipment
- mixer: bottom stirring, 150 l (duplicator), stainless steel EXTRA S
- vibrating screen: stainless steel, 150 mesh
- rotary air pump: rotor diameter 150 mm
- turbostirrer: ULTRA TURAX (Janke-Kunkel) beaker: 5 l
- pH meter PICCOLO
- thermocouple thermometer Procedure 30 g of N-HANCE 3000 were placed into and 5 l beaker and 3 l of demineralised water 2 µS were added. Contents of the beaker were intensely stirred for 30 minutes. The pH value was adjusted to less than 4.5 by addition of an acetic acid solution leading to a viscosity rise.

60 l of demineralised water 2 µS were introduced into a mixer. Then 3 kg of $CaCl_2.6H_2O$ anal.grade were added and the contents heated up to a temperature of 50° C. under stirring. On dissolution of the calcium chloride the stirring was interrupted and 2.7 kg of the raw oxidised cotton wool were introduced. The mixer was closed and the contents were agitated for 120 seconds. Then the pH value of the contents was adjusted by addition of a 20% solution of $Na_2CO_3$ to 6–6.5 and 13 kg of $H_2O_2$ 30% were introduced. The fibre suspension was slowly agitated for 10 minutes. Then the pH value was readjusted to 4.5–5.0 and the prepared viscous solution of N-HANCE 3000 was introduced. The contents of the mixer were stirred intensely for 30 seconds. Subsequently 60 l of synthetic rectified ethanol conc. 98% were introduced into the mixer. After another 15 seconds from adding the ethanol the contents of the mixer were transferred onto a vibrating screen, and the supernatant. Liquid was filtered off. The filtration cake was redispersed in the mixer in 60 l of a mixture of 18 l of synthetic rectified ethanol conc. 98% and 42 l of demineralised water 2 µS. The fibre suspension was filtered again on the vibrating screen.

The isolated material thus prepared may further serve to prepare final products of the nonwoven type via a wet or dry process.

Analysis
- Ca content 4.0% b/w
- Na content 1.8% b/w
- $\Sigma C=O$ content 0.0% b/w
- COOH content 20.7% b/w

Example 2

Material
- oxidised short-fibre cotton (Linters-Temming), (proprietary)
- $C_6OOH$ 16.8% b/w
- ash content <0.15% b/w
- $\Sigma C=O$ 2.6% b/w
- 20% solution $Na_2CO_3$ (Lachema, a.s. Neratovice)
- $CaCl_2.6H_2O$ anal.grade (Lachema, a.s. Neratovice)
- redistilled water (PhBs 1997)
- ethanol, synthetic rectified conc. 98% (Chemopetrol Litvinov, a.s.)
- isopropanol 99.9% (Neuberg Bretang)
- $H_2O_2$ anal.grade 30% (Lachema, a.s. Neratovice)
- gelatine (PhBs 1997)

Equipment
- turbostirrer: ULTRA TURAX (Janke-Kunkel)
- sulphonation flask 1 l
- heater 1.5 kW
- laboratory centrifuge: 4000 rpm
- thermostated water bath
- pH meter PICCOLO
- glass thermometer
- rotary vacuum dryer or hot-air dryer Procedure Into a 1 l sulphonation flask equipped with a turbostirrer and a heater, 400 ml of redistilled $H_2O$ were placed, 15.73 g of $CaCl_2.6H_2O$ were added and on dissolution, 40.0 g of 20% $Na_2CO_3$ solution were introduced under stirring. Subsequently, 50 g of oxidised Linters were added to the white emulsion formed and the contents were heated up to 95° C. and the stirring intensity set to a maximum. After 10 minutes, 30 g of 30% $H_2O_2$ were added into the flask and the hydrolysis continued for another 10 minutes. The contents were then cooled down to 60° C. on a water bath and the pH of the system was adjusted to a value of 4.5–5.0 by addition of 20% solution of $Na_2CO_3$. Furthermore, gelatine solution (10 g of gelatine in 70 g of redistilled $H_2O$) warmed up to 50° C. was added and let to react for another 20 minutes. The flask contents were then cooled down to 30° C. in a water bath and 626 ml of synthetic rectified ethanol conc. 98% were added gradually under intense stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

Analysis
- content Ca 4.4% b/w
- content Na 2.7% b/w
- content $\Sigma C=O$ 0.0% b/w
- content COOH 20.5% b/w
- content N 1.8% b/w

Example 3

Material oxidised short-fibre cotton (Linters -Temming) (proprietary)
$C_6OOH$ 16.8% b/w
ash content <0.15% b/w
$\Sigma C=O$ 2.6% b/w NaOH anal.grade (Lachema, a.s. Neratovice)

redistilled water (PhBs 1997)

ethanol, synthetic rectified conc. 98% (Chemopetrol Litvinov, a.s.)

isopropanol 99.9% (Neuberg Bretang)

$H_2O_2$ anal.grade 30% (Lachema, a.s. Neratovice)

gelatine (PhBs 1997)

Equipment turbostirrer: ULTRA TURAX (Janke-Kunkel)
sulphonation flask 1 l
heater 1.5 kW
laboratory centrifuge: 4000 rpm
thermostated water bath
pH meter PICCOLO
glass thermometer
rotary vacuum dryer or hot-air dryer Procedure Into a 1 l sulphonation flask equipped with a turbostirrer and a heater, 400 ml of redistilled $H_2O$ were placed, and 8 g of NaOH were added. On dissolution, 50 g of oxidised Linters were added, the contents were heated up to 70° C. and the stirring intensity set to a maximum. After 20 minutes, 40 g of 30% $H_2O_2$ were added into the flask, temperature was increased to 85° C., and maintained for another 10 minutes. The contents were then cooled down to 50° C. on a water bath and gelatine solution (10 g of gelatine in 70 g of redistilled H20) warmed up to 50° C. was added to the hydrolysate. The temperature was decreased to 25–30° C. and the pH of the system was checked and adjusted to a value of 6.0–6.5. Subsequently, 626 ml of synthetic rectified ethanol conc. 98% were added gradually under intense stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

Analysis

Na content 3.8% b/w
$\Sigma C=O$ content 0.0% b/w
COOH content 21.5% b/w
N content 2.7% b/w

Example 4

Material oxidised short-fibre cotton (Linters -Temming) (proprietary)
$C_6OOH$ 16.8% b/w
ash content <0.15% b/w
$\Sigma C=O$ 2.6% b/w 20% solution $Na_2CO_3$ (Lachema, a.s. Neratovice)

$CaCl_2.6H_2O$ anal.grade (Lachema, a.s. Neratovice)

redistilled water (PhBs 1997)

ethanol, synthetic rectified conc. 98% (Chemopetrol Litvinov, a.s.)

isopropanol 99.9% (Neuberg Bretang)

$H_2O_2$ anal.grade 30% (Lachema, a.s. Neratovice)

chitosan, degree of deacetylation 92% (Henkel)

Equipment turbostirrer: ULTRA TURAX (Janke-Kunkel)
sulphonation flask 1 l
heater 1.5 kW
laboratory centrifuge: 4000 rpm
thermostated water bath
pH meter PICCOLO
glass thermometer
rotary vacuum dryer or hot-air dryer Procedure Into a sulphonation flask, 250 ml redistilled $H_2O$ were placed, and 5 g of NaOH were added. On dissolution, 25 g of oxidised Linters were introduced under stirring, the temperature increased to 50° C. and the stirring intensity set to a maximum. After hydrolysing for 15 minutes, 35 g of 30% $H_2O_2$ were gradually added to the system and the temperature was maintained at 50° C. for another 20 minutes. The content were cooled down to 30° C. and 400 g of highly viscous 5% solution of chitosan were added. The flask contents were then intensely stirred for another 10 minutes, and the pH of the system was adjusted, by addition of NaOH, to a value of 7.0. Subsequently 300 ml of synthetic rectified ethanol conc. 98% were added under stirring. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for microembolisation, for preparation of haemostatic dusting powders, for manufacture of polymer drugs, e.g. based on cytostatics, or for preparation of spheric particles for macroembolisation.

Analysis

Na content 1.8% b/w
$\Sigma C=O$ content 0.0% b/w
COOH content 10.4% b/w
N content 2.8% b/w

Example 5

Material oxidised short-fibre cotton (Linters-Temming) (proprietary)
$C_6OOH$ 16.8% b/w
ash content <0.15% b/w
$\Sigma C=O$ 2.6% b/w NaOH anal.grade (Lachema, a.s. Neratovice)

HCl 39% anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)
Ambroxol (H. Mack, Germany)

Equipment turbostirrer: ULTRA TURAX (Janke-Kunkel)
sulphonation flask 2 l
heater 1.5 kW
laboratory centrifuge: 4000 rpm
laboratory pin mill ALPINE (35 000 rpm)
thermostated water bath
pH meter PICCOLO
glass thermometer
rotary vacuum dryer or hot-air dryer Procedure Into a sulphonation flask, 400 ml redistilled $H_2O$ were placed, and 8 g of NaOH were added. On dissolution, 50 g of oxidised Linters were introduced under stirring, the temperature increased to 70° C. and the stirring intensity was set to a maximum. After hydrolysing for 20 minutes, 40 g of 30% $H_2O_2$ were gradually added to the system and the temperature was increased to, and maintained at, 85° C. for another 10 minutes. The content were cooled down to 50° C. in a water bath, and gelatine solution (2 g of gelatine in 70 g of redistilled 20) warmed up to 50° C. was added to the hydrolysate. The temperature was decreased to 25–30° C. and the pH of the system was checked and adjusted to a value of 1.6–1.8 by addition of 39% HCl. Under intense stirring, a solution of Ambroxol (25g of ambroxolium hydrochloride in 500 ml of redistilled $H_2O$) was added gradually. After agitating for 5 minutes the pH value was adjusted to 4.3–4.6 by adding 5% NaOH solution, and 626 ml of synthetic rectified ethanol conc. 98% were added under intense stirring. The suspension of Ambroxol containing IMC thus formed was isolated using a laboratory centrifuge. The supernatant liquid was filtered away and the cake was redispersed into, subsequently, 800 ml of 60% ethanol and 250 ml of 98% ethanol, wherein it was let to stay for a minimum of 10 hours. The system was centrifuged again and the product was dried at 40° C. in a rotary vacuum dryer or a hot-air dryer. A white to slightly yellowish powder was obtained and further desagglomerated on an Alpine pin mill.

The product serves for the preparation of a mucoregulatory drug with a prolonged action.

Analysis

Na content 4.6% b/w
$\Sigma C=O$ content 0.0% b/w
COOH content 14.8% b/w
N content 1.9% b/w

Example 6

Material oxidised short-fibre cotton (Linters-Temming) (proprietary)
$C_6OOH$ 16.8% b/w
ash content <0.15% b/w
$\Sigma C=O$ 2.6% b/w
20% solution $Na_2CO_3$ (Lachema, a.s. Neratovice)
$CaCl_2.6H_2O$ anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)
gentamycin sulphate (MERCK)

Equipment turbostirrer: ULTRA TURAX (Janke-Kunkel)
sulphonation flask 2 l
heater 1.5 kW
laboratory centrifuge: 4000 rpm
laboratory pin mill ALPINE (35 000 rpm)
thermostated water bath
pH meter PICCOLO
glass thermometer
hot-air dryer
lyophiliser (Leibold Heraus, Germany)

Procedure

Into a 2 l sulphonation flask equipped with a turbostirrer and a heater, 400 ml of redistilled $H_2O$ were placed, 15.73 g of $CaCl_2.6H_2O$ were added and on dissolution, 40.0 g of 20% $Na_2CO_3$ solution were introduced under stirring. Subsequently, 50 g of oxidised Linters were added to the white emulsion formed and the contents were heated up to 95° C. and the stirring intensity set to a maximum. After 10 minutes, 30 g of 30% $H_2O_2$ were added into the flask and the hydrolysis was continued for another 10 minutes. The contents were then cooled down to 60° C. on a water bath and the pH of the system was adjusted to a value of 4.5–5.0 by addition of 20% solution of $Na_2CO_3$. Furthermore, gelatine solution (10 g of gelatine in 70 g of redistilled $H_2O$) warmed up to 50° C. was added and let to react for another 20 minutes. The flask contents were then cooled down to 30° C. in a water bath and 40 g of gentamycin sulphate in 600 ml of redistilled $H_2O$ were added gradually within 10 minutes. 626 ml of synthetic rectified ethanol conc. 98% were then added gradually under intense stirring to the antibiotic containing IMC suspension formed. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, for the manufacture of a dusting powder or a powder spray for the treatment of infected wounds.

Analysis

Ca content 2.4% b/w
Na content 1.6% b/w
$\Sigma C=O$ content 0.0% b/w
COOH content 9.6% b/w
N content 2.7% b/w

Example 7

Material long-fibre cotton–medicinal cotton wool oxidised by $N_xO_y$ (proprietary)
$C_6OOH$ 18.8% b/w
ash content <0.1% b/w
$\Sigma C=O$ 0.6% b/w
20% solution $Na_2CO_3$ (Lachema, a.s. Neratovice)

CaCl$_2$.6H$_2$O anal.grade (Lachema, a.s. Neratovice)
demineralised water 2 μS
ethanol, synthetic rectified conc. 98% (Chemopetrol Litvinov, a.s.)
isopropanol 99.9% (Neuberg Bretang)
acid acetic anal.grade (Lachema, a.s. Neratovice)
H$_2$O$_2$ anal.grade 30% (Lachema, a.s. Neratovice)
N-HANCE 3000 guargumhydroxypropyltriammoniumchloride
(Aqualon-Hercules)
polybren (hexadimethrindibromide) (FLUKA)
chlorhexidindigluconate Equipment
  mixer: bottom stirring, 150 l (duplicator), stainless steel EXTRA S
  vibrating screen: stainless steel, 150 mesh
  rotary air pump: rotor diameter 150 mm
  turbostirrer: ULTRA TURAX (Janke-Kunkel)
  beaker: 5 l
  pH meter PICCOLO
  thermocouple thermometer Procedure
  30 g of N-HANCE 3000 were placed into and 5 l beaker and 3 l of demineralised water 2 μS were added. Contents of the beaker were intensely stirred for 30 minutes. The pH value was adjusted to less than 4.5 by addition of an acetic acid solution leading to a viscosity rise.
  60 l of demineralised water 2 μS were introduced into a mixer. Then 3 kg of CaCl$_2$.6H$_2$O anal.grade were added and the contents heated up to a temperature of 50° C. under stirring. On dissolution of the calcium chloride the stirring was interrupted and 2.7 kg of the raw oxidised cotton wool were introduced. The mixer was closed and the contents were agitated for 120 seconds. Then the pH value of the contents was adjusted by addition of a 20% solution of Na$_2$CO$_3$ to 6–6.5 and 13 kg of H$_2$O$_2$ 30% were introduced. The fibre suspension was slowly agitated for 10 minutes. Then the pH value was readjusted to 4.5–5.0 and the prepared viscous solution of N-HANCE 3000 was introduced. The contents of the mixer were stirred intensely for 30 seconds. A solution of 35 g of chlorhexidine digluconate in 350 ml of demineralised water 2 μS was then introduced slowly within 10 minutes. Within another 10 minutes, a solution of polybren containing 120 g of polybrenu in 1000 ml of demineralised water 2 μS was added. Subsequently 60 l of synthetic rectified ethanol conc. 98% were introduced into the mixer. After another 15 seconds from adding the ethanol, the contents of the mixer were transferred onto a vibrating screen, and the supernatant. Liquid was filtered off. The filtration cake was redispersed in the mixer in 60 l of a mixture of 18l of synthetic rectified ethanol conc. 98% and 42 l of demineralised water 2 μS. The fibre suspension was filtered again on the vibrating screen.
  The isolated material thus prepared may further serve to prepare, via a wet or dry process, final products of the nonwoven type having an enhanced haemostatic activity and a bactericidal effect.

Analysis
  Ca content 3.6% b/w
  Na content 1.9% b/w
  ΣC=O content 0.0% b/w
  COOH content 18.1% b/w
  N content 0.35% b/w Example 8

Material
  oxidised short-fibre cotton (Linters-Temming) (proprietary)
  C$_6$OOH 16.8% b/w
  ash content <0.15% b/w
  ΣC=O 2.6% b/w
  20% solution Na$_2$CO$_3$ (Lachema, a.s. Neratovice)
  CaCl$_2$.6H$_2$O anal.grade (Lachema, a.s. Neratovice)
  redistilled water (PhBs 1997)
  ethanol, synthetic rectified conc. 98% (Chemopetrol Litvinov, a.s.)
  isopropanol 99.9% (Neuberg Bretang)
  H$_2$O$_2$ anal.grade 30% (Lachema, a.s. Neratovice)
  Chitosan, degree of deacetylation 92% (Henkel)
  Clarithromycin lactobionan (Abbott Laboratories, Italy)

Equipment
  turbostirrer: ULTRA TURAX (Janke-Kunkel)
  sulphonation flask 1 l
  heater 1.5 kW
  laboratory centrifuge: 4000 rpm
  thermostated water bath
  pH meter PICCOLO
  glass thermometer
  rotary vacuum dryer or hot-air dryer
  dialysing bag (regenerated cellulose)
  lyophiliser (Leybold Heraus, Germany)
  laboratory pin mill ALPINE (35 000 rpm)

Procedure
  Into a sulphonation flask, 250 ml redistilled H$_2$O were placed, and 5 g of NaOH were added. On dissolution, 25 g of oxidised Linters were introduced under stirring, the temperature increased to 50° C. and the stirring intensity set to a maximum. After hydrolysing for 15 minutes, 35 g of 30% H$_2$O$_2$ were gradually added to the system and the temperature was maintained at 50° C. for another 20 minutes. The content were cooled down to 30° C. and 400 g of highly viscous 2% solution of chitosan, having a pH value of 3.5, were added. The flask contents were then intensely stirred for another 10 minutes, and the pH of the system was adjusted, by addition of NaOH, to a value of 7.0. During another 10 minutes, a solution of clarithromycin (44 g of clarithromycin in 456 ml of redistilled H$_2$O) was introduced and the pH of the system was adjusted to a value of 7.0–7.5. Stirring was interrupted, the flask contents were transferred into a dialysing bag and dialysed against water for 48 hours. Subsequently the product was isolated by centrifugation, lyophilised, and disintegrated on the laboratory pin mill ALPINE.
  The product can be used, for instance, to prepare tablets or granules efficient against Helicobacter pylori occurring in the gastrointestinal tract.

Analysis
  Na content 4.8% b/w
  ΣC=O content 0.0% b/w
  COOH content 18.8% b/w
  N content 0.7% b/w Example 9

Material
  oxidised short-fibre cotton (Linters-Temming) (proprietary)
  C$_6$OOH 16.8% b/w ash content <0.15% b/w
ΣC=O 2.6% b/w
NaOH anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)
$Bi(NO_3)_3.5H_2O$ (MERCK)

Equipment turbostirrer: ULTRA TURAX (Janke-Kunkel)
sulphonation flask 2 l
heater 1.5 kW
laboratory centrifuge: 4000 rpm
thermostated water bath
pH meter PICCOLO
glass thermometer
rotary vacuum dryer or hot-air dryer Procedure Into a sulphonation flask, 400 ml redistilled $H_2O$ were placed, and 8 g of NaOH were added. On dissolution, 50 g of oxidised Linters were introduced under stirring, the temperature increased to 70° C. and the stirring intensity was set to a maximum. After hydrolysing for 20 minutes, 40 g of 30% $H_2O_2$ were gradually added to the system and the temperature was increased to, and maintained at, 85° C. for another 10 minutes. The content were cooled down to 50° C. in a water bath, and gelatine solution (0.5 g of gelatine in 50 ml of redistilled $H_2O$) warmed up to 50° C. was added to the hydrolysate. The temperature was decreased to 25–30° C. and the pH of the system was checked and adjusted to a value of 1.6–1.8 by addition of 39% HCl. A freshly prepared solution of $BiNO_3$ (54 g of $BiNO_3.5H_2O$ in 746 ml of $H_2O$) was introduced and the temperature maintained for another 15 minutes. Then the temperature was decreased to 25–30° C. and the pH of the system was checked and readjusted to a value of 5.5–6.0. 626 ml of synthetic rectified ethanol conc. 98% were then added gradually under intense stirring to the formed. The $BiO^+$ containing IMC suspension thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for a minimum of 4 hours. It was then centrifuged again, redispersed into 99.9% isopropanol, and let to stay for a minimum of 10 hours at 20° C. The suspension formed was then centrifuged again and the product was dried in a rotary vacuum dryer or a hot-air dryer.

The product can be used, for instance, to prepare dusting powders for wound treatment or tablets for treatment of gastrointestinal tract malfunctions.

Analysis

Na content 1.9% b/w
ΣC=O content 0.0% b/w
COOH content 20.0% b/w
N content <0.3% b/w
Bi content 4.7% b/w Example 10

Material oxidised short-fibre cotton (Linters-Temming) (proprietary)
$C_6OOH$ 16.8% b/w
ash content <0.15% b/w
ΣC=O 2.6% b/w
20% solution $Na_2CO_3$ (Lachema, a.s. Neratovice)
$CaCl_2.6H_2O$ anal.grade (Lachema, a.s. Neratovice)
redistilled water (PhBs 1997)
ethanol, synthetic rectified conc. 98% (Chemopetrol Litvinov, a.s.)
isopropanol 99.9% (Neuberg Bretang)
$H_2O_2$ anal.grade 30% (Lachema, a.s. Neratovice)
gelatine (PhBs 1997)
cimetidine hydrochloride (SPOFA)

Equipment turbostirrer: ULTRA TURAX (Janke-Kunkel)
sulphonation flask 2 l
heater 1.5 kW
laboratory centrifuge: 4000 rpm
thermostated water bath
pH meter PICCOLO
glass thermometer
rotary vacuum dryer or hot-air dryer Procedure Into a 1 l sulphonation flask equipped with a turbostirrer and a heater, 400 ml of redistilled $H_2O$ were placed, 15.73 g of $CaCl_2.6H_2O$ were added and on dissolution, 40.0 g of 20% $Na_2CO_3$ solution were introduced under stirring. Subsequently, 50 g of oxidised Linters were added to the white emulsion formed and the contents were heated up to 95° C. and the stirring intensity set to a maximum. After 10 minutes, 30 g of 30% $H_2O_2$ were added into the flask and the hydrolysis was continued for another 10 minutes. The contents were then cooled down to 60° C. on a water bath and the pH of the system was adjusted to a value of 4.5–5.0 by addition of 20% solution of $Na_2CO_3$. Furthermore, gelatine solution (10 g of gelatine in 70 g of redistilled $H_2O$) warmed up to 50° C. was added and let to react for another 20 minutes. The flask contents were then cooled down to 30° C. in a water bath and a solution of cimetidine (36 g of cimetidine hydrochloride in 400 ml of redistilled $H_2O$) were added under intense stirring. The contents were intensely agitated for 10 minutes and 800 ml of synthetic rectified ethanol conc. 98% were then added gradually. The suspension of IMC thus formed was isolated using a laboratory centrifuge. The supernatant liquid was filtered away and the cake was redispersed into 250 ml of 50% ethanol. The system was centrifuged again and after the separation of the supernatant liquid, the IMC was redispersed into 250 ml of synthetic rectified ethanol conc. 98% and let to stay for 4 hours. It was then centrifuged again, redispersed into 99.9% isopropanol, and let to stay for a minimum of 10 hours at 20° C. The gel formed was centrifuged again and the product was dried in a rotary vacuum dryer or a hot-air dryer.

The product can be used, for instance, to manufacture tablets or granulates for the treatment of the gastrointestinal tract or other non-malignant ulcerations.

Analysis

Ca content 4.4% b/w
Na content 2.7% b/w
ΣC=O content 0.0% b/w

COOH content 20.5% b/w
N content 2.1% b/w

Example 11

Material

IMC-MDOC complex (as per above Example 2)
[(2S;2R)-3-amino-2-hydroxy4-phenylbutenoyl]-L-leucin (Bestatin)
(Boehringer Mannheim, Germany)
redistilled water (PhBs 1997)
methanol, conc. anal.grade (Chemopetrol Litvinov, a.s.)
diethylether (Lachema, a.s. Neratovice)

Equipment turbostirrer: ULTRA TURAX (Janke-Kunkel)
sulphonation flask 2 l
laboratory centrifuge: 4000 rpm
hot-air dryer Procedure The IMC-MDOC complex as prepared in Example 2 above was redispersed into redistilled water in a sulphonation flask using a turbostirrer. A solution of Bestatin in methanol was then added to the flask in an amount sufficient to yield a 10% b/w concentration of Bestatin in the resulting Bestatin-gelatine-MDOC complex. After thorough homogenisation, the suspension formed was isolated by centrifugation. The supernatant liquid was filtered away and the filtration cake was redispersed into concentrated methanol again, centrifuged, redispersed in diethylether, and after being allowed to stay for 1 hour, it was dried in a hot-air dryer.

The product, a microdispersed form of a Bestatin-gelatine-MDOC complex, can be used, for instance, to prepare microembolisation agents used in regional chemotherapy of malignant tumours or flat dressing structures for wound treatment.

EXAMPLE A

Preparation of Tablets and Pellets from MDOC

MDOC=Microdispersed Oxidised cellulose

Material

MDOC (Ca/Na salt of PAGA), particle size 0.1–2.0 µm, specific surface area 86 $m^2/g$, COOH group content 22.2% b/w, Ca content 4.2% b/w, Na content 3.8% b/w Equipment tabletting machine (KORSCH EK 0, Berlin)

Procedure 100 g of MDOC were introduced into the tabletting machine. The tabletting force was set at a value of 5 kN.

Result

The tablets prepared were smooth and cohesive and had a weight of 0.5 g. Disintegration rate of the tablets in a saline F1/1 was 15 minutes at 20° C., and 8 minutes at 37° C.

APPLICATION EXAMPLE

A patient aged 55, displaying an increased cholesterol content in blood was treated by MDOC tablets administered orally for 50 days, at a dose of 6 tablets daily. After the treatment both LDL content and total cholesterol content were significantly reduced.

| Blood analysis: | before treatment | after treatment |
| --- | --- | --- |
| Total Cholesterol | 8.60 mmol/l | 6.60 mmol/l |
| HDL | 1.16 mmol/l | 1.20 mmol/l |
| LDL | 6.50 mmol/l | 4.90 mmol/l |
| Triacylglycerols | 2.70 mmol/l | 2.40 mmol/l |

EXAMPLE B

Preparation of Tablets and Pellets from IMC-MDOC Complex

Material

IMC-MDOC complex-see Example 2 (of ALPE01/C)
magnesium stearate (SIGMA)
ascorbic acid (MERCK)
α-tocoferol acetate (Slovakofarma Hlohovec)
ethanol synthetic rectified (Chemopetrol Litvinov, a.s.)

Equipment tabletting machine (KORSCH EK 0, Berlin)
blender (Nautamix 300)
counter-flow drier (BINDER)

Procedure 10 kg of IMC-MDOC complex of composition according to Example 2 were placed into the blender. 660 g of micronised ascorbic acid, 1660 g of α-tocoferol acetate emulgated in 2500 ml of ethanol and 1000 g of magnesium stearate were added. The mixture was homogenised for 3 hours and dried in a counter-flow drier at a temperature of 50° C. until the ethanol was removed.

100 g of the resulting dry powder were introduced into the tabletting machine. The tabletting force was set at a value of 7 kN.

Result

The tablets prepared were smooth and cohesive and had a weight of 0.5 g. Disintegration rate of the tablets in a saline F1/1 was 17 minutes at 20° C., and 8 minutes at 37° C.

Application Example

A patient aged 57, displaying an increased cholesterol content in blood was treated by MDOC tablets administered orally for 50 days, at a dose of 6 tablets daily. After the treatment both LDL content and total cholesterol content were significantly reduced.

| Blood analysis: | before treatment | after treatment |
| --- | --- | --- |
| Total Cholesterol | 7.70 mmol/l | 5.70 mmol/l |
| HDL | 1.16 mmol/l | 1.30 mmol/l |
| LDL | 4.40 mmol/l | 3.30 mmol/l |
| Triacylglycerols | 1.81 mmol/l | 1.80 mmol/l |

EXAMPLE C

Preparation of Granules in a Fluid Bed

Material

MDOC, particle size 0.1–2.0 µm, specific surface area 86 $m^2/g$, COOH group content 22.2% b/w, Ca content 4.2% b/w, Na content 3.8% b/w Equipment set of vibrating screens with mesh size 100, 150, 200, 250, 350, 500 µm
mixer, bottom agitated, vessel size 1000 ml, 8000 rpm, equipped with a nozzle for inlet of the granulation medium counter-flow drier (BINDER)

Procedure 100 g of MDOC were placed into the mixer, the mixer was closed and the agitation begun. A water mist was gradually injected into the mixer at a rate of 10 g/45 seconds. The granulate formed was transferred to the counter-flow drier and dried at a temperature of 45° C. until the humidity content was reduced to below 6% b/w. The dried granules were sieve-screened using the set of vibrating screens. The individual fractions were packaged into glass vials in amounts of 0.5–2.0 g each as required. The preparation was sterilised by γ irradiation with a dose of 25 kGy.

Indication

The product may be used as a) an embolisation agent, or b) an antilipemicum.

EXAMPLE D

Preparation of Granules from IMC-MDOC Complex

Material

IMC-MDOC complex-see Example 2

Equipment set of vibrating screens with mesh size 100, 150, 200, 250, 350, 500 µm mixer, bottom agitated, vessel size 1000 ml, 8000 rpm, equipped with a nozzle for inlet of the granulation medium counter-flow drier BINDER Procedure 100 g of MDOC were placed into the mixer, the mixer was closed and the agitation begun. Saturated water vapour was gradually injected into the mixer at a rate of 10 g/45 seconds. The granulate formed was transferred to the counter-flow drier and dried at a temperature of 45° C. until the humidity content was reduced to below 6% b/w. The dried granules were sieve-screened using the set of vibrating screens. The individual fractions were packaged into glass vials in amounts of 0.5–2.0 g each as required. The preparation was sterilised by γ irradiation with a dose of 25 kGy.

Indication

The product may be used as a) an embolisation agent, or b) an antilipemicum.

The invention is not limited to the embodiments hereinbefore described which may be varied in detail.

What is claimed is:

1. An antilipemic composition including a biocompatible anionic polyanhydroglucuronic acid or salt thereof which is that of a partially or completely hydrolyzed and oxidative-environment neutralized polyanhydroglucuronic acid containing material.

2. A composition as claimed in claim 1 wherein the polyanhydroglucuronic acid or salt thereof is derived from a starch, cellulose or gum, or is of microbial origin.

3. A composition as claimed in claim 1 wherein the polyanhydroglucuronic acid or salt thereof includes a biocompatible salt thereof, a copolymer thereof or a biocompatible intermolecular complex thereof.

4. A composition as claimed in claim 3 wherein the biocompatible intermolecular polymer complex is a complex of:
an anionic component comprising polyanhydroglucuronic acid or salt, which is that of a partially or completely hydrolysed and oxidative-environment hydrolysed polyanhydroglucuronic acid containing material; and
a non protein cationic component comprising a linear or branched natural, semi-synthetic or synthetic oligomer or polymer.

5. A composition as claimed in claim 4 wherein at least 5% of the basic structural units of the anionic component are glucuronic acid.

6. A composition as claimed in claim 4 wherein the cationic component contains nitrogen that either carries a positive charge or wherein a positive charge is induced by contact with the polysaccharidic anionic component.

7. A composition as claimed in claim 6 wherein the cationic component is a member selected from the group consisting of a derivative of acrylamide, a derivative of methacrylamide, a copolymer of acrylamide and a copolymer of methacrylamide.

8. A composition as claimed in claim 6 wherein the cationic component is a member selected from the group consisting of polyacrylamide, a copolymer of hydroxyethylmethacrylate and hydroxypropylmethacrylamide, and a copolymer of acrylamide, butylacrylate, maleicanhydride and methylmethacrylate.

9. A composition as claimed in claim 4 wherein the cationic component is a cationised natural polysaccharide.

10. A composition as claimed in claim 9 wherein the polysaccharide is a starch, cellulose or gum.

11. A composition as claimed in claim 10 wherein the gum is guargumhydroxypropyltriammonium chloride.

12. A composition as claimed in claim 4 wherein the cationic component is a synthetic or semi-synthetic polyamino acid.

13. A composition as claimed in claim 12 wherein the cationic component is a member selected from the group consisting of polylysin, polyarginin and α,β-poly-[N-(2-hydroxyethyl)-DL-aspartamide].

14. A composition as claimed in claim 4 wherein the cationic component is a synthetic anti-fibrinolytic.

15. A composition as claimed in claim 14 wherein the anti-fibrinolytic is a hexadimethrindibromide.

16. A composition as claimed in claim 4 wherein the cationic component is a natural or semi-synthetic peptide.

17. A composition as claimed in claim 16 wherein the peptide is a member selected from the group consisting of a protamine, gelatine, fibrinopeptide, and a derivative of one of the foregoing.

18. A composition as claimed in claim 4 wherein the cationic component is an aminoglucane or derivative thereof.

19. A composition as claimed in claim 18 wherein the aminoglucane is fractionated chitin or its de-acetylated derivative chitosan.

20. A composition as claimed in claim 18 wherein the aminoglucane is of microbial origin or is isolated from an arthropod shell.

21. A composition as claimed in claim 3 wherein the polyanhydroglucuronic acid includes a biocompatible salt or copolymer thereof.

22. A composition as claimed in claim 3 wherein the polyanhydroglucuronic acid and salt thereof contain in their polymeric chain from 8 to 30 percent by weight of carboxyl groups, at least 80 percent by weight of these groups being uronic groups, at most 5 percent by weight of carbonyl groups, and at most 0.5 percent by weight of bound nitrogen.

23. A composition as claimed in claim 22 wherein the polyanhydroglucuronic acid and salt thereof contain in their polymeric chain at most 0.2 percent by weight of bound nitrogen.

24. A composition as claimed in claim 22 wherein the molecular mass of the polymeric chain of the polyanhydroglucuronic acid and salt thereof is from $1 \times 10^3$ to $3 \times 10^5$ Daltons.

25. A composition as claimed in claim 24 wherein the molecular mass of the polymeric chain of the anionic component ranges from $5 \times 10^3$ to $1.5 \times 10^5$ Daltons.

26. A composition as claimed in claim 22 wherein the content of carboxyl groups is in the range of from 12 to 26 percent by weight, at least 95 percent of these groups being uronic groups.

27. A composition as claimed in claim 22 wherein the polyanhydroglucuronic acid and salt thereof contain at most 1 percent by weight of carbonyl groups.

28. A composition as claimed in claim 22 wherein each carbonyl group is an intra- or intermolecular 2,6 or 3,6 hemiacetal, a 2,4-hemialdal or a C2–C3 aldehyde.

29. A composition as claimed in claim 4 wherein the cationic component is gelatine.

30. A composition as claimed in claim 4 wherein the cationic component is chitosan.

31. A composition as claimed in claim 1 which includes at least one biocompatible biologically active substance.

32. A composition as claimed in claim 1 which includes at least one biologically acceptable adjuvant.

33. A composition as claimed in claim 1 which includes a pharmaceutically active adjuvant.

34. A composition as claimed in claim 33 wherein the adjuvant is an antilipemic agent.

35. A composition as claimed in claim 34 wherein the antilipemic agent is a phospholipid.

36. A composition as claimed in claim 1 in an oral administration form.

37. A composition as claimed in claim 36 in the form of a tablet, pellet, capsule, granule or microsphere.

* * * * *